(12) United States Patent
Liu

(10) Patent No.: US 10,779,748 B2
(45) Date of Patent: Sep. 22, 2020

(54) BIOMETRIC ELECTROMYOGRAPHY SENSOR DEVICE FOR FATIGUE MONITORING AND INJURY PREVENTION AND METHODS FOR USING SAME

(71) Applicant: IFGCURE HOLDINGS, LLC, Los Angeles, CA (US)

(72) Inventor: Stephen H Liu, Los Angeles, CA (US)

(73) Assignee: IFGCURE HOLDINGS, LLC, Los Angeles, CA (US)

( * ) Notice: Subject to any disclaimer, the term of this patent is extended or adjusted under 35 U.S.C. 154(b) by 0 days.

(21) Appl. No.: 16/512,260

(22) Filed: Jul. 15, 2019

(65) Prior Publication Data
US 2020/0015700 A1    Jan. 16, 2020

Related U.S. Application Data

(60) Provisional application No. 62/698,165, filed on Jul. 15, 2018.

(51) Int. Cl.
*A61B 5/00*  (2006.01)
*A61B 5/0488*  (2006.01)
*A61B 5/04*  (2006.01)
*A61B 5/024*  (2006.01)

(52) U.S. Cl.
CPC ........ *A61B 5/0488* (2013.01); *A61B 5/04012* (2013.01); *A61B 5/7264* (2013.01); *A61B 5/02405* (2013.01); *A61B 5/6804* (2013.01); *A61B 5/7203* (2013.01); *A61B 5/7275* (2013.01); *A61B 2562/0219* (2013.01)

(58) Field of Classification Search
CPC ..... A61B 5/11; A61B 5/1123; A61B 5/04012; A61B 5/0488; A61B 5/7264; A61B 5/7203; A61B 5/7275; A61B 5/02405; A61B 5/6804; A61B 2562/0219
See application file for complete search history.

(56) References Cited

U.S. PATENT DOCUMENTS

| | | | |
|---|---|---|---|
| 6,708,051 B1 * | 3/2004 | Durousseau | A61B 5/0478 600/383 |
| 9,782,122 B1 * | 10/2017 | Pulliam | A61B 5/4824 |
| 2005/0283205 A1 * | 12/2005 | Lee | A61B 5/0488 607/48 |
| 2008/0058668 A1 | 3/2008 | Momen | |

(Continued)

FOREIGN PATENT DOCUMENTS

WO    2012040388    3/2012

*Primary Examiner* — Max F Hindenburg
(74) *Attorney, Agent, or Firm* — Ferguson Case Orr Paterson

(57) ABSTRACT

The present device is directed to a biometric electromyography (EMG) sensor device and methods for using the same to provide a user with the ability to monitor physical muscle fatigue and protect themselves against injury due to overuse. Embodiments of the present disclosure include an accelerometer for artifact noise removal and an EMG sensor that is used to collect EMG signals and surface EMG (sEMG) signals from electrodes placed onto a wearable device, which can be in tight contact with the skin due to its elasticity. This collected data can then be transmitted to an electronic device via a microcontroller. The electronic device may include an app that is continuously running to monitor user fatigue in real-time.

13 Claims, 4 Drawing Sheets

(56) References Cited

U.S. PATENT DOCUMENTS

| | | | | |
|---|---|---|---|---|
| 2014/0135593 A1* | 5/2014 | Jayalth | ............... | A61B 5/0022 |
| | | | | 600/301 |
| 2015/0351690 A1* | 12/2015 | Toth | .................. | A61B 5/6833 |
| | | | | 600/373 |
| 2018/0184907 A1* | 7/2018 | Tran | .................. | G06F 19/3418 |
| 2019/0290181 A1* | 9/2019 | Mrvaljevic | .......... | A61B 5/0205 |

* cited by examiner

BIOMETRIC ELECTROMYOGRAPHY SENSOR DEVICE FOR FATIGUE MONITORING AND INJURY PREVENTION AND METHODS FOR USING SAME

RELATED APPLICATION

This application claims the benefit of priority of U.S. Provisional Application No. 62/698,165 entitled WEARABLE ELECTROMYOGRAPHY SENSOR DEVICE FOR CONTINUOUS MONITORING OF FATIGUE, filed Jul. 15, 2018. The contents of this application are hereby incorporated by reference herein in their entirety.

FIELD OF THE DISCLOSURE

The present disclosure is related to the field of medical and biometric devices, especially wearable devices, and methods for injury prevention and data monitoring such as fatigue monitoring.

BACKGROUND OF THE DISCLOSURE

Wearable technologies have grown as an industry as recent health trends have incentivized fitness tracking. These products have been designed to help users quantify their level of physical activity. Current wearable technology trackers include EMG sensors, heart rate monitors, and accelerometers—with some companies even using blood oxygen saturation detectors. The current market, however, fails to capture a valuable use case for the average consumer and instead is too heavily skewed towards the clinical field, failing to fulfill the purpose of generating widespread, easily accessible data that all users are able to easily interpret. For instance, with the exception of specific users, the data provided by current trackers is often too difficult for most to interpret. The data is just not user-friendly, and one would need the help of a professional to make sense of the pure numbers, as data requires further analysis. As an example, measurements provided by heart rate or blood saturation monitors may provide useful results for clinical purposes; however, such monitors have limited consumer uses. In a clinical setting, heart rate monitors may be used in tandem with electrocardiography (EKG) sensors in order to gauge left-right heart contractions. This task is performed continuously during most operations in order to monitor vital bodily functions. In the consumer market, however, heart rate monitors are used either continuously or are aggregated over a period of time to determine physical body stress. Data shown in these monitors is effective at determining cardiovascular stress, but the data is indeterminate of the activity and does not provide consumers easy access to understanding the data.

Many large companies, such as Apple, Google, and Samsung, have designed fitness and health trackers. Products such as digital watches and cell phones are configured and designed to be used in tandem with user collected data such as sleep or exercise duration. As a result, users may get frustrated with having to manually input data in order to receive results that can presumably be automatically generated. To solve this problem, new companies, such as FitBit, have begun developing hardware to help supplement data collection via heart rate monitors and sleep trackers that automates a process that users previously needed to manually undergo. In a similar fashion, Athos, another wearable technology company, is seeking to equip athletes with the ability to view real-time muscle activity that is automatically generated and collected through software/hardware. Athos has focused on left-right muscle balance to help athletes maintain balanced muscle growth as well as improve athletes' form. Similar to the above companies, Athos values collecting user data, but it falls short in that the data generated is too simplistic. Athos' product design is not centered around users; while information on left-right muscle balance can be important, for the typical user, it does not warrant the expensive price of Athos equipment. In addition, Athos created a system that measures muscle fatigue based on duration and number of contractions; this system is not based on biologically driven factors but rather on pre-set inputs, leading to inaccuracies. Further adding to the non-user centric design, Athos products have bulky material that isn't conducive to being carried around.

U.S. Patent Publication No. 2008/0058668 to Momen et al. discloses a method for enabling muscle signals that correspond to muscle contractions to be mapped to one or more functions of an electronic device such as a prosthetic device or gaming apparatus. The disclosure in this publication focuses on muscle signal classification, but fails to provide methods for using muscle signals to monitor levels of fatigue. Rather, it uses the classifications for control purposes.

PCT International Publication No. WO 2012/040388 to Grey et al. discloses a muscle assessment method for utilizing a computing system, surface EMG (sEMG) sensors, and other sensors to gather data for subjects engaged in an activity and assessing muscle condition, muscle activity, and statistically related averages. Although fatigue is assessed, it is done so continuously and determined by plotted data points fit to a curve. Unlike the present disclosure, this method does not isolate individual movements and provide specific fatigue levels for each movement.

The market still has plenty of room for growth as medical and biometric devices become more portable. The overall pain point in the industry has been providing user-centric design. Many of the sensors used in these devices have medical purposes, such as testing for anemia or monitoring a patient's heart rate during operations; however, these operations may not be useful for the general consumer.

Accordingly, the present disclosure is aimed at solving these and other problems discussed below.

SUMMARY OF THE DISCLOSURE

It is an object of devices and methods of the present disclosure to provide an EMG sensor and wearable technology that focuses on muscle fatigue and muscle activation.

Embodiments of the present disclosure are related to wearable sensor technology or "smart clothing." Specifically, embodiments of the present disclosure are directed to wearable sensor technology including a portable and wearable electromyography (EMG) sensor that is configured to continually monitor electrical signals for local muscle fatigue and methods for using the same.

It is very useful for an athlete to measure muscle fatigue. Fatigue has not been a main focus in the consumer-driven EMG market. Using EMG signals to measure muscle fatigue requires extensive analysis of EMG signals and has only been performed in clinical studies. One of the greatest obstacles for researchers has been differentiating between definitive muscle contractions and normal user movement. Previous studies have resolved this problem by designing their analysis around one specific type of muscle contraction, such as bicep curls. The action is then performed in a repetitive nature at specific intervals in order to separate data. Embodiments of the present disclosure are not muscle- or movement-specific and can be used to measure fatigue for any muscle in the body.

It is an object of embodiments of the present disclosure to mitigate and remove noise in order to separate significant motion and muscle contractions from casual movement and to collect and record this data.

It is another object of embodiments of the present disclosure to determine and monitor short-term and long-term fatigue and their effect on athletes' performance and recovery.

It is an object of embodiments of the present disclosure to determine muscle activation and report this data to the user in real-time via a graphical user interface such as an easily digestible smartphone app or a similar method.

It is an object of embodiments of the present disclosure to determine muscle activation based on contractions over a threshold voltage.

It is an object of embodiments of the present disclosure to further the analysis of fatigue measurements and provide consumer-oriented data.

Objects of certain embodiments of the disclosure are achieved by providing a fatigue monitoring device, comprising: one or more electrodes; an EMG sensor connected to said one or more electrodes; and an accelerometer, wherein said monitoring device is configured to be worn by a user.

Objects of other embodiments of the disclosure are achieved by providing a wearable EMG device for measuring muscle fatigue, comprising: a garment including one or more electrodes; an EMG sensor integrated into the garment; and a microcontroller.

In certain embodiments, the microcontroller is configured to include Bluetooth capability.

In certain embodiments, the device includes a lithium polymer battery.

In certain embodiments, the lithium polymer battery is configured to be charged wirelessly.

In certain embodiments, the device will measure muscle fatigue based on time-frequency parameters of the power spectrum of the signal.

In certain embodiments, the device emits final output data, helping the average consumer make sense of when they are fatigued.

In certain embodiments, the device is configured to assist a wearer to protect himself against injury due to overuse of the muscle.

In certain embodiments, the device uses wireless and/or microUSB charging to power itself.

In certain embodiments, the device removes insignificant muscle data (i.e., motion artifacts and insignificant noise).

In certain embodiments, the device will analyze fatigue of distinct muscle motion, contractions, and/or movements.

In certain embodiments, the device will provide fatigue feedback to the user.

In certain embodiments, the device will repeat the process of analyzing and providing fatigue feedback until workout completion.

Other objects of the disclosure are achieved by providing a non-transitory computer readable storage medium storing a computer program product to analyze sensor data, the non-transitory computer readable storage medium configured to analyze data provided by the device.

Other objects of the disclosure are achieved by providing a smartphone app configured to analyze data provided by the device described throughout the specification.

Other objects of the disclosure are achieved by providing a smartphone app for analyzing sensor data transmitted while using wearable EMG sensors, the smartphone app comprising code that takes data and turns it into a visual representation of fatigue as measured by different color combinations and shades. For example, green could represent the lowest amount of fatigue, yellow could represent a moderate amount of fatigue, and red could represent the highest amount of fatigue.

Other objects of the disclosure and its particular features and advantages will become more apparent from consideration of the following drawings and accompanying detailed description. It should be understood that the detailed description and specific examples, while indicating the preferred embodiments of the disclosure, are intended for purposes of illustration only and are not intended to limit the scope of the disclosure.

DETAILED DESCRIPTION OF THE DISCLOSURE

Figure 1:
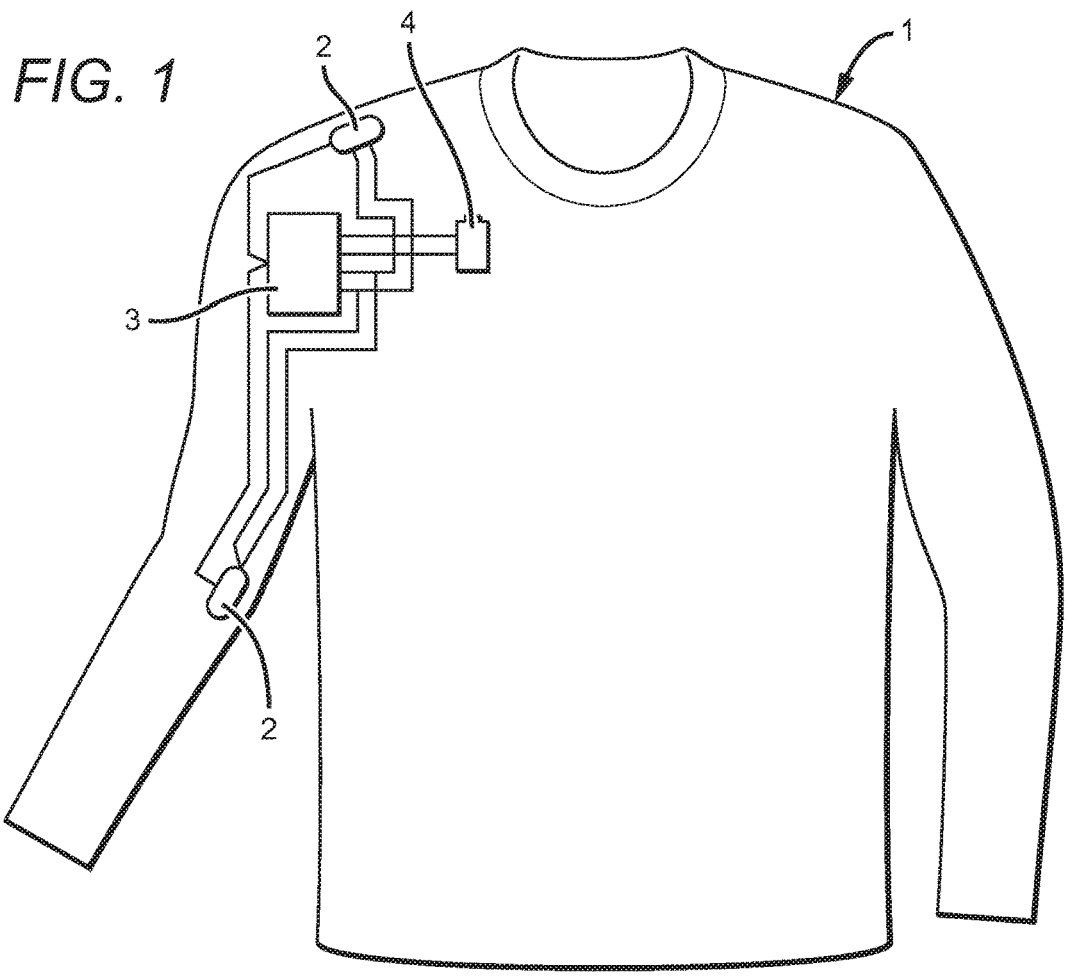
FIG. 1 depicts electrical devices embedded into a garment in an embodiment of the disclosure.

Embodiments of the present disclosure provide a way to measure and monitor muscle fatigue in athletes and the general fitness consumer. Some embodiments may be comprised of a wearable device with conductive electrodes. In certain embodiments, the wearable device comprises a garment such as conductive smart clothing, braces, or tape with a certain level of elasticity sufficient to provide correct placement and attachment of the electrodes without the need of a health professional. In some embodiments, the garment comprises conductive materials, such as copper, that are interwoven into the seams of the garment to create electrical pathways for signals to travel. The electrodes can be integrated into the garment and may be button electrodes and/or comprise a rubber material to further adhere to the user and maintain correct placement throughout an exercise. After the garment is placed over the muscles of interest, an EMG sensor, such as a MyoWare™ muscle sensor, detects contractions, amplifies the signal and sends the EMG signals (for example, through wiring in the garment) to an Arduino Pico microcontroller, connected to a Bluetooth, for example, HC-06. The microcontroller acts as an analog to digital converter (ADC). It will receive and send the incoming signal in real-time to a smartphone app via Bluetooth protocol or other transfer protocol.

In certain embodiments, this collected data is transmitted to an electronic device via a microcontroller directly. The electronic device includes an app that is continuously running for real-time monitoring as the user fatigues. A battery will be used in tandem with both microUSB and wireless charging. In one embodiment, the casing can be mounted onto the area behind the shoulder blade to reduce intrusion on the user's movement, for example a pitching motion.

In certain embodiments, the app will then preprocess the signal using analog and/or digital filters to reduce noise. Once filtered, the signal can be classified based on a long short-term memory (LSTM) neural network to indicate percent fatigue (displayed on the app).

In certain embodiments, T=time-frequency parameters (instantaneous mean frequency, median frequency, etc.) of the signal power spectrum are used as features to train the neural network, and such parameters have been shown to correlate with muscle fatigue.

One method according to the present disclosure for monitoring muscle fatigue comprises the steps of: providing a user with a wearable device; defining one or more movements determined by measurements taken from the device; classifying each movement into a class of activities; and determining a fatigue level for each movement.

In some embodiments, the wearable device can comprise an accelerometer, one or more electrodes, and an EMG sensor connected to the electrodes for recording EMG signals and/or sEMG signals taken from the user.

In some embodiments, the accelerometer can be used to define one or more movements. This defining step from the above method for monitoring fatigue is intended as a noise artifact removal step and may further comprise the step of using the accelerometer to measure the total distance that the wearable device travels from a start point of a motion determined by an increase in velocity above a threshold value to an end point of the motion determined by a decrease in velocity below a threshold value and determining whether the motion is an artifact by comparing the total distance measurement to a set of training data. If it is determined that the motion is an artifact, then the data is removed.

If it is determined that the motion is not an artifact, then it may be a movement and the defining step may further comprise the step of using the accelerator to measure the time duration from the start point to the end point of the motion and determining whether the motion is an artifact by comparing the time duration of the motion to the training data. If it is determined that the motion is an artifact, then the data is removed.

If it is determined that the motion is not an artifact, then it may be a movement and the defining step may further comprise the step of using the accelerator to measure the initial position and/or orientation of the wearable device and determining whether the motion is an artifact by comparing the initial position and/or orientation of the motion to the training data. If it is determined that the motion is an artifact, then the data is removed.

If it is determined that the motion is not an artifact, then it may be a movement and the defining step may further comprise the step of using the accelerator to measure the change in acceleration of the wearable device from the start point to the end point and determining whether the motion is an artifact by comparing the change in acceleration to the training data. If it is determined that the motion is an artifact, then the data is removed.

If it is determined that the motion is not an artifact after the final step, then it is considered a movement. It is contemplated that the final determination of a movement may occur at the end of any of the steps discussed above or at the end of other steps. It is further contemplated that the order of the steps discussed above may be rearranged and/or some may be omitted; for example, the step of measuring the initial position and/or orientation of the device may occur first and the step of measuring change in acceleration may not occur at all.

The training data set discussed above may come from a variety of sources. For example, the training data set could have been collected from a plurality of previously collected measurements from prior motions generated by the user. Also, the training data set could have been collected from a pool of previously collected measurements from prior motions generated by other users. The training data set could also comprise a combination user specific and non-user specific data. Further, the training data set could be dynamic such that the initial data is non-user specific, but as the user records more data, the training data set becomes more heavily influenced by the user specific data. Generally, the more user specific data that is recorded in the training data set, the more customized the device will be for that particular user.

The method for monitoring fatigue may further comprise classifying the movement into a class of activities once the movement is defined. For example, the movement may be classified as a fastball pitch or a changeup pitch. Other examples of activities may include, without limitation, a bicep curl, a push up, a kick, a step, a swimming stroke, a golf swing, a kettlebell swing, etc. This movement classification step may be accomplished by analyzing one or more of the measurements described above gathered by the accelerometer. For example, the movement classification step may comprise comparing the initial position measurement and/or the change in acceleration measurement to the training data.

The method for monitoring fatigue may further comprise determining a fatigue level for the movement by taking some or all of the following measurements from the EMG signals: short-term rate of change of instantaneous mean frequency; activity-specific long-term rate of change of instantaneous mean frequency; total long-term rate of change of instantaneous mean frequency; short-term rate of change of power output; and long-term rate of change of power output.

In some embodiments, the power output measurements may be gathered by converting the EMG signal data to the frequency domain and/or taking the root mean squared (RMS) of the EMG signal data.

Once these EMG measurements are gathered, features may be extracted from each measurement as part of a machine learning algorithm and statistical model that can ultimately classify each movement into one of a plurality of fatigue levels and monitor user fatigue. These features may be compared with a second training data set and considered equally or weighted differently.

Similar to the first training data set, the second training data set may comprise previously recorded user specific EMG data, a pool of previously recorded non-user specific EMG data, or a combination of both. Where user specific data is used, the device may be calibrated by assessing the user's maximum contraction velocity and maximum power output to determine the percentage of maximum power that the user is producing.

In some embodiments of the disclosure, only some of these features may be considered and/or other features may be considered. For example, one embodiment will extract five features (one from each of the above EMG measurements) and weigh each feature equally in classifying fatigue level.

In another embodiment, the same five features will be extracted, but they will be weighed in the following order from a most important to a least important, here: short-term rate of change of instantaneous mean frequency; activity-specific long-term rate of change of instantaneous mean frequency; short-term rate of change of power output; long-term rate of change of power output; total long-term rate of change of instantaneous mean frequency.

In still another embodiment, only the feature extracted from the short-term rate of change of instantaneous mean frequency will be considered.

In some embodiments, the short-term rate of change of instantaneous mean frequency and the short-term rate of change of power output are measured over the time duration of the movement (i.e., the time duration of the motion discussed above). Over this time duration, the EMG signal may be split into intervals of time (e.g., 10-200 ms), and the intervals can be compared to each other.

In some embodiments, the activity-specific long-term rate of change of instantaneous mean frequency and the long-term rate of change of power output are measured over the course of an entire exercise that comprises a plurality of movements. For these measurements, subsequent movements that have been classified under the same activity can be compared to each other. For example, the instantaneous mean frequency of a first movement that has been classified as a particular activity (e.g., fastball pitch) can be compared to the instantaneous mean frequency of a second movement that has also been classified as the same activity (e.g., fastball pitch). Likewise, the power output of a first movement that has been classified as a particular activity (e.g., changeup pitch) can be compared to the power output of a second movement that has also been classified as the same activity (e.g., changeup pitch).

The use of the term "exercise" herein is not meant as limiting. It is contemplated that one exercise may or may not occur in one setting, day, or even year. For example, one exercise may comprise all of the pitches that a pitcher throws to a single batter. Another exercise may comprise all of the pitches that a pitcher throws throughout an inning or an entire game. Yet another exercise may comprise all of the pitches that a pitcher throws throughout a season or even over a decade-long career.

In some embodiments, the total instantaneous mean frequency is measured across all movements comprised within an exercise, regardless of whether they are classified as the same activity. For example, the instantaneous mean frequency of a first movement that has been classified as a particular activity (e.g., fastball pitch) can be compared to the instantaneous mean frequency of a second movement that has also been classified as the same activity (e.g., fastball pitch) and to the instantaneous mean frequency of a third movement that has been classified as a different activity (e.g., changeup pitch) but was still performed during the same exercise (e.g., throughout the ninth inning of a baseball game).

Although many of the examples above relate to pitching motion, applications of the present disclosure are not limited to baseball. For example, a weightlifter generates repetitive motion that could be defined as movements that could be classified as various activities over the course of an exercise. A movement could be defined as a single repetition during a workout. The activities could include various lifts such as a bicep curl, bench press, or squat. As discussed above, an "exercise" could be defined broadly depending on the length of fatigue monitoring. For example, an exercise could be defined as a single set of eight to ten repetitions. An exercise could also be defined as an entire workout comprising multiple sets of different lifts. An exercise could further be defined as multiple workouts performed over the course of a week, month, or year.

This measure of fatigue is a biologically driven measure from EMG and sEMG signals as opposed to other methods that use predetermined measurements.

Figure 2:
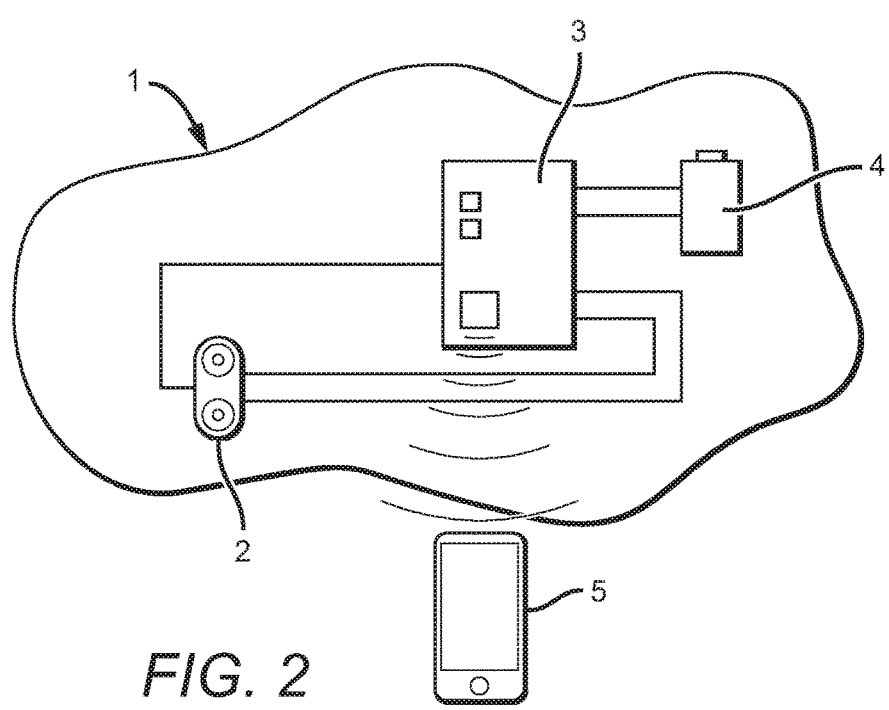
FIG. 2 depicts a close-up view of the electrical components of FIG. 1.

Referring to FIGS. 1-2, the conductive garment 1 is designed with the specific placement of electrodes over the shoulder rotator cuff, scapular rotators, forearm muscles, neck muscles, and/or spinal muscles. The electrodes will be connected directly to a MyoWare™ Sensor 2 to detect surface EMG (sEMG) signals. The analog signals will be sent through the conductive garment to an Arduino Pico microcontroller 3, where the signals will be amplified and converted to a digital signal. Furthermore, the microcontroller will then transfer the digital EMG signals to a smartphone app 5 using Bluetooth or other transfer capabilities. The app will process and analyze the sEMG signal to monitor percent muscle fatigue. The microcontroller and MyoWare sensor are powered externally by a 3.7V 2500 mAh lithium polymer battery 4.

Figure 3:
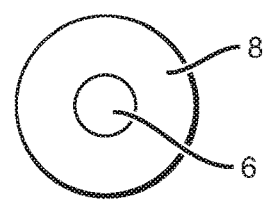
FIG. 3 depicts an electrode that may be attached to a garment.
Figure 4:
FIG. 4 depicts snap buttons that may be used to attach an electrode to a garment.

Referring to FIGS. 3-4, electrode 6 may comprise rubber grip material 8 for gripping in proper placement on a user's body. Electrode 6 may also attach to a garment via snap buttons 10.

Figure 5:
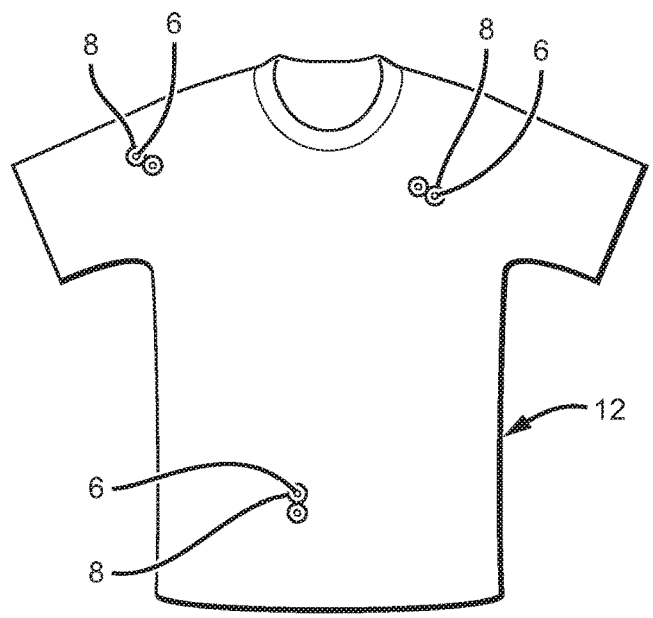
FIG. 5 depicts a shirt with multiple electrodes attached thereto.

FIG. 5 shows one embodiment of the disclosure, where electrodes 6 are attached to shirt 12. Rubber grip 8 allows electrodes 6 to remain adhered to a user's body in a proper location, for example here, on the user's shoulder rotator cuff.

Figure 6:
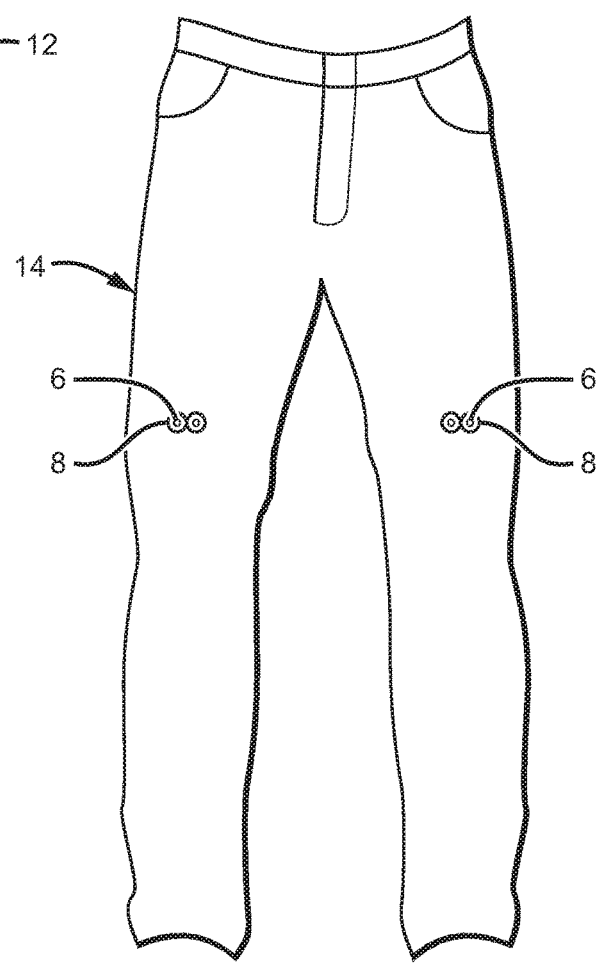
FIG. 6 depicts a pair of pants with multiple electrodes attached thereto.

FIG. 6 shows another embodiment of the disclosure, where electrodes 6 are attached to pants 14. Rubber grip 8 allows electrodes 6 to remain adhered to a user's body in a proper location, for example here, on the user's quadriceps.

Figure 7:
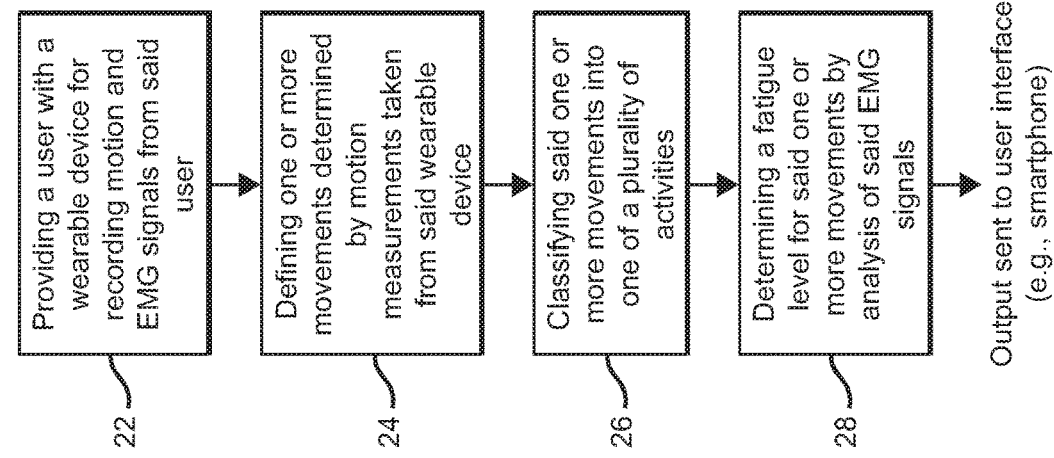
FIG. 7 depicts one method of monitoring fatigue according to the present disclosure.

FIG. 7 shows one method for monitoring fatigue according to the present disclosure, wherein the first step 22 is providing a user with a wearable device for recoding motion and EMG signals from the user. In one embodiment, motion is recorded using an accelerometer, and EMG signals are recored using one or more electrodes in connection with an EMG sensor. The second step 24 is defining one or more movements taken from the wearable device, which could be defined from measurements recorded from the accelerometer. The third step 26 is classifying the one or more movements into one of a plurality of activities, for example, a fastball pitch or a changeup pitch. The fourth step 28 is determining a fatigue level for the one or more movements, which can be determined by an analysis of the EMG signals. After determining fatigue levels for the one or more movements, this information can be sent to a graphical user interface such as an application on a smartphone.

Figure 8:
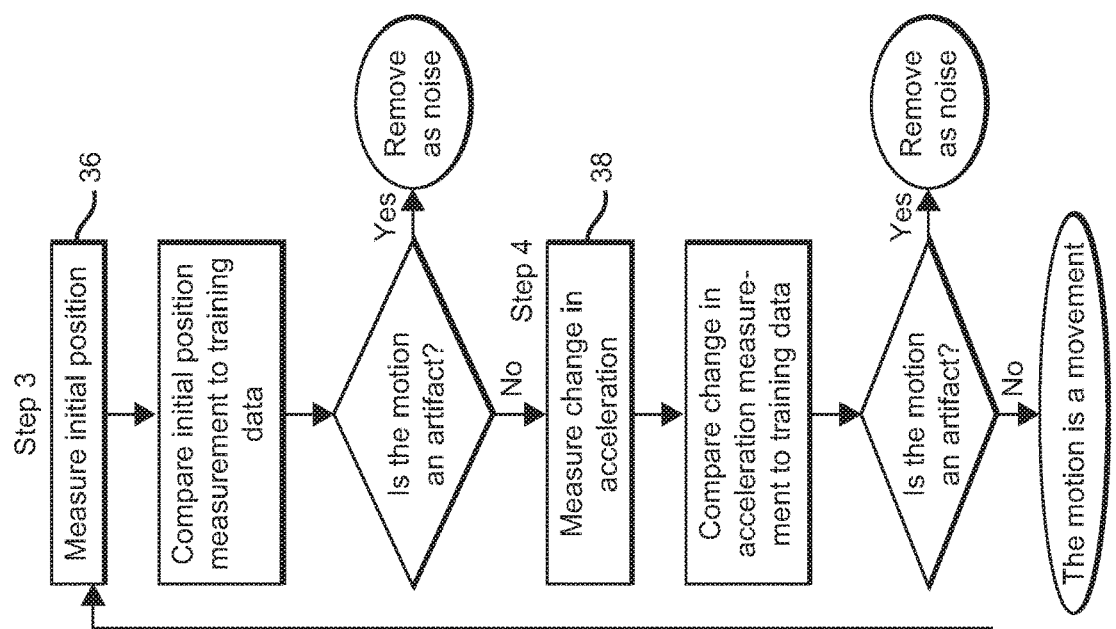
FIG. 8 depicts one method for defining one or more movements according to the present disclosure.
Figure 9:
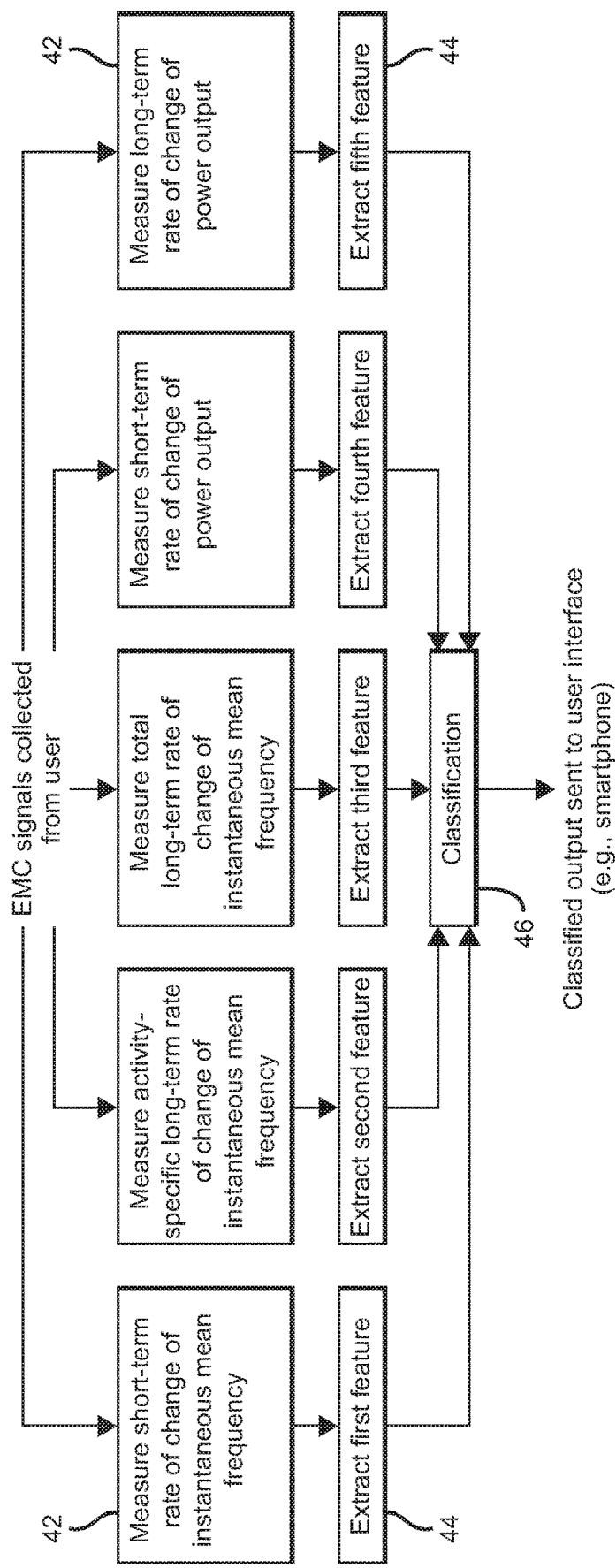
FIG. 9 depicts one method for determining levels of fatigue according to the present disclosure.

FIG. 8 shows one method for defining one or more movements according to the present disclosure, wherein an accelerometer is applied to a user to take various motion measurements. The first step 32 is to measure a total distance traveled during the motion and compare the total distance traveled measurement to a set of training data. Based on this comparison, the motion is either removed as a noise artifact or the method continues to the second step 34. The second step 34 measures a time duration of the motion and compares the time duration to the set of training data. Based on this comparison, the motion is either removed as a noise artifact or the method continues to the third step 36. The third step 36 measures an initial position and/or orientation and compares this initial position and/or orientation measurement to the set of training data. Based on this comparison, the motion is either removed as a noise artifact or the method continues to the fourth step 38. The fourth step 38 measures a change in acceleration, and compares the change in acceleration measurement to the set of training data. After the fourth step 38, the motion is either removed as a noise artifact or defined as a movement. It is understood that in other embodiments, some or all of these steps may occur in a different order and that this list of steps may be nonexclusive of other possible steps. Once defined, the movement may be classified, for example, by a machine learning algorithm FIG. 9 shows one method for determining levels of fatigue according to the present disclosure. In this method, five different measurements 42 are taken from EMG signals that are collected from a user, including: short-term rate of change of instantaneous mean frequency; activity-specific long-term rate of change of instantaneous means frequency; total long-term rate of change of instantaneous mean frequency; short-term rate of change of power output; and long-term rate of change of power output. It is understood that these measurements may be taken in any order or all at the same time. From these measurements 42, five features 44 are extracted, corresponding to each of the measurements 42. These features 44 are then used during a classification step 46 through a comparison to a set of training data. The classification step 46 may be achieved through a machine learning algorithm that is, for example, designed to prevent injuries.

Having thus described several embodiments for practicing the inventive method, its advantages and objectives can be easily understood. Variations from the description above may and can be made by one skilled in the art without departing from the scope of the disclosure.

Accordingly, this disclosure is not to be limited by the embodiments as described, which are given by way of example only and not by way of limitation.

What is claimed is:

1. A method for monitoring fatigue, comprising:
   providing a user with a wearable device comprising:
      an accelerometer;
      one or more electrodes; and
      an EMG sensor connected to said one or more electrodes for recording EMG signals from said user;
   defining one or more movements by:
   measuring with said accelerometer a total distance traveled of said wearable device from a start point of a motion determined by an increase in velocity above a threshold value to an end point of said motion determined by a decrease in velocity below a threshold value;
   determining that said motion is not an artifact by comparing said total distance traveled to at least one total distance traveled measurement comprised in a first training data set;
   measuring with said accelerometer a time duration from said start point to said end point of said motion;
   determining that said motion is not an artifact by comparing said time duration to at least one time duration measurement comprised in said first training data set;
   measuring with said accelerometer at least one position of said wearable device;
   determining that said motion is not an artifact by comparing said at least one position to at least one position measurement comprised in said first training data set;
   measuring with said accelerometer a change in acceleration of said wearable device from said start point to said end point of said motion; and
   determining that said motion is a first movement by comparing said change in acceleration to at least one change in acceleration measurement comprised in said first training data set;
   classifying said first movement into one of a plurality of activities by comparing said at least one position to said first training data set and comparing said change in acceleration to said first training data set such that a first activity comprises said first movement;
   determining a fatigue level for said first movement by:
      measuring a short-term rate of change of instantaneous mean frequency from said EMG signals over said time duration of said motion;
      extracting a first feature based on said short-term rate of change of instantaneous mean frequency;
      measuring an activity-specific long-term rate of change of instantaneous mean frequency from said EMG signals over a duration of an exercise comprising said first movement and at least a second movement by comparing instantaneous mean frequency of said first movement to instantaneous mean frequency of at least said second movement, wherein said first activity further comprises said second movement;
      extracting a second feature based on said activity-specific long-term rate of change of instantaneous mean frequency;
      measuring a total long-term rate of change of instantaneous mean frequency from said EMG signals over a duration of said exercise by comparing instantaneous mean frequency of said first movement to instantaneous mean frequency of at least said second movement and a third movement, wherein said exercise further comprises said third movement and wherein said first activity does not comprise said third movement;
      extracting a third feature based on said total long-term rate of change of instantaneous mean frequency;
      measuring a short-term rate of change of power output from said EMG signals over said time duration of said motion;
      extracting a fourth feature based on said short-term rate of change of power output;
      measuring a long-term rate of change of power output from said EMG signals over said duration of said exercise by comparing power output of said first movement to power output of at least said second movement;
      extracting a fifth feature based on said long-term rate of change of power output; and
      classifying said first movement into one of a plurality of fatigue levels by comparing said first, second, third, fourth, and fifth features to a second training data set.

2. The method of claim 1, further comprising displaying a visual representation of said one of a plurality of fatigue levels to said user through a graphical user interface.

3. The method of claim 2, wherein said visual representation is a color selected from the group consisting of red, yellow, or green.

4. The method of claim 1, wherein said first training data set consists of a plurality of prior motions recorded by said user.

5. The method of claim 1, wherein said first training data set consists of a plurality of prior motions not recorded by said user.

6. The method of claim 1, wherein said first training data set comprises a plurality of prior motions, wherein a first portion of said prior motions were recorded by said user and a second portion of said prior motions were not recorded by said user.

7. The method of claim 6, wherein, over time, a ratio of said first portion to said second portion increases.

8. The method of claim 1, wherein the step of classifying said first movement into one of a plurality of activities is achieved by a machine learning algorithm.

9. The method of claim 1, wherein said second training data set consists of a plurality of prior motions recorded by said user.

10. The method of claim 1, wherein said second training data set consists of a plurality of prior motions not recorded by said user.

11. The method of claim 1, wherein said second training data set comprises a plurality of prior motions, wherein a first portion of said prior motions were recorded by said user and a second portion of said prior motions were not recorded by said user.

12. The method of claim 11, wherein, over time, a ratio of said first portion to said second portion increases.

13. The method of claim 1, wherein the step of classifying said first movement into one of a plurality of fatigue levels is determined by a machine learning algorithm.

\* \* \* \* \*